(12) United States Patent
Pham et al.

(10) Patent No.: US 7,265,082 B2
(45) Date of Patent: Sep. 4, 2007

(54) AZEOTROPE-LIKE COMPOSITIONS OF 1,1,1,3,3-PENTACHLOROPROPANE AND CARBON TETRACHLORIDE

(75) Inventors: Hang T. Pham, Amherst, NY (US); Rajiv R. Singh, Getzville, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 450 days.

(21) Appl. No.: 10/911,004

(22) Filed: Aug. 4, 2004

(65) Prior Publication Data

US 2006/0030507 A1  Feb. 9, 2006

(51) Int. Cl.
*C11D 7/50* (2006.01)

(52) U.S. Cl. ............... 510/408; 510/407; 510/411; 510/415

(58) Field of Classification Search ............ None
See application file for complete search history.

(56) References Cited

U.S. PATENT DOCUMENTS

| | | | |
|---|---|---|---|
| 5,710,352 A | 1/1998 | Tung | 570/166 |
| 5,918,481 A | 7/1999 | Pham et al. | 62/631 |
| 6,023,004 A | 2/2000 | Thenappan et al. | 570/188 |
| 6,313,360 B1 * | 11/2001 | Wilson et al. | 570/257 |
| 6,362,383 B1 | 3/2002 | Wilmet et al. | 570/166 |
| 6,452,057 B1 * | 9/2002 | Lambert et al. | 570/172 |
| 6,500,993 B1 * | 12/2002 | Mathieu et al. | 570/127 |
| 6,552,238 B1 * | 4/2003 | Mainz et al. | 570/177 |
| 6,638,987 B2 | 10/2003 | Bogdan et al. | 521/131 |
| 2003/0009066 A1 | 1/2003 | Branam | |
| 2003/0199716 A1 | 10/2003 | Wilson et al. | |
| 2003/0208090 A1 | 11/2003 | Baker, et al. | |

* cited by examiner

*Primary Examiner*—Gregory Webb
(74) *Attorney, Agent, or Firm*—Colleen D. Szuch

(57) ABSTRACT

The invention relates to azeotropic and azeotrope-like mixtures of 1,1,1,3,3-pentachloropropane (HCC-240fa) and carbon tetrachloride and a process for separating the azeotrope-like mixtures. The compositions of the invention are useful as an intermediate in the production of HFC-245fa. The latter is useful as a nontoxic, zero ozone depleting fluorocarbon useful as a solvent, blowing agent, refrigerant, cleaning agent and aerosol propellant.

19 Claims, No Drawings

AZEOTROPE-LIKE COMPOSITIONS OF 1,1,1,3,3-PENTACHLOROPROPANE AND CARBON TETRACHLORIDE

FIELD OF THE INVENTION

The present invention relates to azeotropic and azeotrope-like compositions of 1,1,1,3,3-pentachloropropane (HCC-240) and carbon tetrachloride.

BACKGROUND

Fluorocarbon based fluids have found widespread use in industry in a number of applications, including as refrigerants, aerosol propellants, blowing agents, heat transfer media, and gaseous dielectrics. Because of the suspected environmental problems associated with the use of some of these fluids, it is desirable to use fluids having low or even zero ozone depletion potential, such as hydrofluorocarbons ("HFCs") and hydrochlorofluorocarbons ("HCFCs").

As is known, fluorochemicals are frequently included as a component in blowing agents utilized in the manufacture of various synthetic plastic formed products. For many years CFC-11 was a very important product in this market. In recent years, however, CFC-11 has frequently been replaced by the bridge-fluorocarbon HCFC-141b. More recently, a need has arisen (caused at least in part by government regulation) for foam manufacturers to discontinue use of the HCFC-141b by the end of the year 2003 in favor of even more desirable HFC products.

One HFC, which has become commercially important as a replacement for environmentally deficient products, such as HCFC-141b, is the HFC 1,1,1,3,3-pentafluoropropane ("HFC-245fa"). Many processes for producing HFC-245fa involve the use of the HCC 1,1,1,3,3-pentachloropropane ("HCC-240fa") as a reactant. For example, U.S. Pat. No. 6,023,004, which is assigned to the assignee of the present invention and which is incorporated herein by reference, describes the liquid phase catalytic fluorination of 1,1,1,3,3-pentachloropropane to HFC-245fa.

Thus, because of the importance of HFC-240fa as a feedstock in the production of HFC-245fa, improvements in the processes used to produce HCC-240fa can have a positive impact on the development of HFC replacements for products, which are not environmentally desirable.

U.S. Pat. No. 6,313,360 describes a process for producing HCC-240fa by first reacting carbon tetrachloride ($CCl_4$) and vinyl chloride in the presence of a catalyst mixture comprising organophosphate solvent, iron metal and ferric chloride under conditions sufficient to produce a product mixture containing HCC-240fa. The product mixture is then fractionated such that a tops fraction enriched in HCC-240fa is separated from the product mixture and a bottoms fraction results, which comprises the iron metal/ferric chloride catalyst components and heavy end by-products. A portion of the bottoms fraction is recycled to the reactor. Other processes produce similar reaction product streams.

Because carbon tetrachloride is a reactant in such processes, it is common that the reaction product mixture will contain HCC-240fa and carbon tetrachloride. These components typically will be contained in a light fraction from one or more of the fractionation steps described in the prior art. As described in detail hereinafter, applicants have discovered that certain combinations of HCC-240fa and carbon tetrachloride exhibit the unique and unpredictable property of azeotropy, and applicants have therefore come to appreciate a need for improved processes directed specifically to the production of HCC-240fa and/or HFC-245fa. In addition, HCC-240fa may be present as a reaction product in many fluorination reactions directed to the production of other fluorinated compounds. Thus, applicants have come to appreciate and need more generally for improved processes directed to the production of HFCs and HCFCs.

SUMMARY OF THE INVENTION

Applicants have discovered the existence of azeotrope and azeotrope-like compositions comprising HCC-240fa and carbon tetrachloride. Moreover, applicants have discovered improved processes for the production of HCC-240fa and/or HFC-245fa. In preferred embodiments, the processes comprise reacting carbon tetrachloride and vinyl chloride to produce a reaction product mixture comprising HCC-240fa and carbon tetrachloride. In one preferred embodiment of the method aspects of the present invention, the present azeotrope and azeotrope-like compositions are separated from the reaction mixture, and optionally but preferably the component parts thereof are thereafter separated to produce compositions enriched in HFC-240fa, enriched in $CCl_4$, or both. As used herein, the reference to enriched refers to the component having a higher concentration in the enriched composition relative to the concentration of that component in the azeotrope or azeotrope-like composition.

The azeotrope-like compositions are useful also as solvents, as well as compositions for removing surface oxidation from metals, and in processes for the removal of impurities from HCC-240fa.

DETAILED DESCRIPTION OF PREFERRED EMBODIMENTS

The present inventors have developed several compositions that can help to satisfy the continuing need for substitutes for CFCs and HCFCs. In one embodiment, the present invention provides azeotrope-like compositions comprising 1,1,1,3,3-pentachloropropane ("HCC-240fa") and carbon tetrachloride ($CCl_4$).

It is known that the composition of an azeotropic mixture varies with pressure variations in that the relative concentrations of the components of the azeotropic mixture will change with pressure. Thus it is possible that two compounds with close boiling points in azeotropic admixture can be separated by distillation, which takes advantage of the pressure variation effect (for example, pressure swing distillation).

The invention also provides a method of forming an azeotropic or azeotrope-like composition, which consists essentially of blending 1,1,1,3,3-pentachloropropane and carbon tetrachloride.

The invention still further provides a process for removing 1,1,1,3,3-pentachloropropane from a mixture containing 1,1,1,3,3-pentachloropropane and at least one impurity, which comprises adding carbon tetrachloride to the mixture in an amount sufficient to form an azeotropic or azeotrope-like composition of the 1,1,1,3,3-pentachloropropane and the carbon tetrachloride, and thereafter separating the azeotropic composition from the impurity.

Compositions

The present compositions are azeotrope-like compositions. As used herein, the term "azeotrope-like" is intended in its broad sense to include both compositions that are strictly azeotropic and compositions that behave like azeotropic mixtures. From fundamental principles, the thermodynamic state of a fluid is defined by pressure, temperature, liquid composition, and vapor composition. An azeotropic mixture is a system of two or more components in which the liquid composition and vapor composition are equal at the stated pressure and temperature. In practice, this means that the components of an azeotropic mixture are constant boiling and cannot be separated during distillation.

Azeotrope-like compositions are constant boiling or essentially constant boiling. In other words, for azeotrope-like compositions, the composition of the vapor formed during boiling or evaporation (under substantially isobaric conditions) is identical, or substantially identical, to the original liquid composition. Thus, with boiling or evaporation, the liquid composition changes, if at all, only to a minimal or negligible extent. This is to be contrasted with non-azeotrope-like compositions in which, during boiling or evaporation, the liquid composition changes to a substantial degree. All azeotrope-like compositions of the invention within the indicated ranges as well as certain compositions outside these ranges are azeotrope-like.

The azeotrope-like compositions of the invention may include additional components that do not form new azeotrope-like systems, or additional components that are not in the first distillation cut. The first distillation cut is the first cut taken after the distillation column displays steady state operation under total reflux conditions. One way to determine whether the addition of a component forms a new azeotrope-like system so as to be outside of this invention is to distill a sample of the composition with the component under conditions that would be expected to separate a non-azeotropic mixture into its separate components. If the mixture containing the additional component is non-azeotrope-like, the additional component will fractionate from the azeotrope-like components. If the mixture is azeotrope-like, some finite amount of a first distillation cut will be obtained that contains all of the mixture components that is constant boiling or behaves as a single substance.

It follows from this that another characteristic of azeotrope-like compositions is that there is a range of compositions containing the same components in varying proportions that are azeotrope-like or constant boiling. All such compositions are intended to be covered by the terms "azeotrope-like" and "constant boiling." As an example, it is well known that at differing pressures, the composition of a given azeotrope will vary at least slightly, as does the boiling point of the composition. Thus, an azeotrope of A and B represents a unique type of relationship, but with a variable composition depending on temperature and/or pressure. It follows that, for azeotrope-like compositions, there is a range of compositions containing the same components in varying proportions that are azeotrope-like. All such compositions are intended to be covered by the term azeotrope-like as used herein.

The present invention provides azeotrope and azeotrope-like compositions comprising 1,1,1,3,3-pentachloropropane and carbon tetrachloride. Preferably, the novel azeotrope-like compositions of the present invention comprise effective amounts of carbon tetrachloride and 1,1,1,3,3-pentachloropropane. The term "effective amounts" as used herein refers to the amount of each component which upon combination with the other component or components, results in the formation of the present azeotrope-like compositions.

The inventive compositions are preferably binary azeotropes, which consist essentially of carbon tetrachloride with 1,1,1,3,3-pentachloropro- pane. In the certain embodiments, the inventive compositions consist essentially of from about 0.01 to about 10 weight percent 1,1,1,3,3-pentachloropropane and from about 99.9 to about 90 weight percent carbon tetrachloride, preferably the inventive compositions consist essentially of from about 0.02 weight percent to about 5 weight percent 1,1,1,3,3-pentachloropropane and about 99.8 to about 95 weight percent carbon tetrachloride. In certain more preferred embodiments, the present compositions consist essentially of about 0.05 weight percent to about 3 weight percent 1,1,1,3,3-pentachloropropane and about 99.5 to about 97 weight percent carbon tetrachloride.

The preferred compositions of the present invention have a vapor pressure of about 14.4 psia to about 14.7 psia at about 78° C. By way of example, an azeotrope-like composition having about 2 weight percent carbon tetrachloride and about 98 weight percent 1,1,1,3,3-pentachloropropane has been found to have a vapor pressure of about 14.4 psia at about 77.7° C.

The Methods

Chlorination and Fluorination Processes

The method aspects of the present invention include improved chlorination processes comprising the steps of (a) reacting one or more reactants to produce a reaction product comprising at least HCC-240fa and $CCl_4$ and removing from said reaction product an azeotrope or azeotrope-like composition comprising HCC-240fa and $CCl_4$. Optionally, but preferably, the methods also include separating at least a portion of the $CCl_4$ from said removed azeotrope or azeotrope-like composition to produce a composition enriched in HCC-240fa. Optionally, but preferably, the methods may also include producing from said azeotrope or azeotrope-like composition a composition enriched in $CCl_4$. When one or more of the optional separations step is used, it is generally preferred that at least a portion of the $CCl_4$ so separated is recycled to the chlorination reaction.

The chlorination step of the present invention can be carried out in accordance with any process known in the art, and particulars of all such processes are within the scope of the present invention and need not be explained in detail here. It is sufficient to note that it is common in well known in such processes that a mixture of halogenated compounds, $CCl_4$ and other byproducts are found in the reaction product stream, and that in at least some of these reaction products both $CCl_4$ and HCC-240fa are present. Thus, the mixture of reactants, byproducts and reaction intermediates of the process may be present along with the $CCl_4$ and HCC-240fa in the mixture.

Accordingly, in one embodiment, the present invention provides a process for separating 1,1,1,3,3- pentachloropropane from a 1,1,1,3,3-pentachloropropane/carbon tetrachloride azeotropic mixture. It will be appreciated by those skilled in the art that several techniques are known and available for separating azeotropic or azeotrope-like compositions into compositions enriched in one or more of the components thereof. The term "enriched" is used herein to refer to the condition during the distillation of a mixture in which the concentration of one component in either the distillate or a bottoms product is higher relative to its concentration in the mixture.

For example, liquid-liquid phase separation techniques are generally effective in this regard and are believed to adaptable for use in accordance with the present invention. In other embodiments, the present process comprises, consists essentially of, or consists of the steps of:

(A) distilling a mixture comprising a mixture of 1,1,1,3, 3-pentachloropropane and carbon tetrachloride at a first pressure to produce a stream comprising an azeotrope-like composition of 1,1,1,3,3-pentachloropropane and carbon tetrachloride; and (B) introducing said azeotropic composition to at least one distillation stage at a second pressure to produce a stream enriched in either 1,1,1,3,3-pentachloropropane or carbon tetrachloride. The distillation steps of the present methods may be performed using a single distillation column or a series of distillation columns. In embodiments wherein a single distillation column is used, the methods of the present invention are typically performed as batch distillations. The mixture may be fed, for example, into a batch distillation column operating at a first pressure. The distillate is then collected and refed into the column at a second pressure. Preferably, the methods of the present invention are performed using a series of distillation columns, meaning at least two columns, operating at different pressures in a batch or continuous distillation. Examples of distillation columns and methods suitable for use in the present invention are disclosed in U.S. Pat. No. 5,918,481 (issued to AlliedSignal), which is incorporated herein by reference.

The temperatures at which these distillations are performed are directly related to the boiling points and pressures used, and are well within the scope of knowledge of one skilled in the art.

In certain other embodiments, the present invention provides a method for removing 1,1,1,3,3-pentachloropropane from a mixture containing 1,1,1,3,3-pentachloropropane and at least one impurity. As used herein, the term "impurity" refers to any compound present in a mixture with 1,1,1,3, 3-pentachloropropane from which it is desirable, for a given application, to separate the 1,1,1,3,3-pentachloropropane. Preferably, the impurity itself does not form an azeotrope-like mixture with 1,1,1,3,3-pentachloropropane, carbon tetrachloride or a mixture of 1,1,1,3,3pentachloropropane and carbon tetrachloride.

The preferred methods for separating 1,1,1,3,3-pentachloropropane and at least an impurity comprises adding carbon tetrachloride to the mixture in an amount sufficient to form an azeotrope-like composition of the 1,1,1,3,3-pentachloropropane and the carbon tetrachloride, and then separating the azeotropic composition from the mixture.

The azeotropic composition of the present invention may be separated from the mixture comprising the impurity by any of a number of conventional methods. Examples of separation methods include, for example, distillation, scrubbing, other art-recognized separating means, and combinations of two or more thereof. Any mixture containing 1,1,1,3,3-pentachloropropane and at least one impurity may be used in the present method. While such mixtures may be provided via any conventional source, in certain preferred embodiments, the mixtures are reaction products resulting from a manufacturing process, most notably, the production of 1,1,1,3,3-pentachloropropane and/or HFC-245fa.

Those of skill in the art will recognize that the amount of carbon tetrachloride to be added to the mixture, and to form an azeotrope-like composition, will depend on the conditions under which the azeotrope-like composition is formed. In light of the disclosure herein, those of skill in the art will be readily able to determine the amounts of carbon tetrachloride necessary to form azeotrope-like compositions with 1,1,1,3,3-pentachloropropane under a wide range of pressures and temperatures.

Uses of the Compositions

The compositions of the present invention may be used in a wide variety of applications as substitutes for CFCs and HCFCs. For example, the present compositions are useful as solvents, blowing agents, refrigerants, cleaning agents and aerosols. In addition, the compositions of the present invention are particularly suited for use in producing relatively pure 1,1,1,3,3-pentachloropropane.

The following non-limiting examples serve to illustrate the invention.

EXAMPLE 1

Binary compositions consisting essentially of 1,1,1,3,3-pentachloropropane (HCC-240fa) and carbon tetrachloride are blended to form homogeneous mixtures having different compositions. The boiling points of the mixtures were measured using a platinum resistance thermometer at 14.45 psia pressure.

Table 1 shows boiling point measurement of 1,1,1,3,3-pentachloropropane and carbon tetrachloride as a function of composition of weight percent 1,1,1,3,3-pentachloropropane at 14.45 psia pressure. From this data it is observed that at 14.45 psia the composition exhibits azeotrope-like properties at about 0.05 to 10 weight percent. Based on further observations made during the experiment, it is determined that the composition at which the boiling point is the minimum is about 1.5 weight percent 1,1,1,3,3-pentachloropropane or between about 0.05 and 2.55 weight percent 1,1,1,3,3-pentachloropropane at 14.45 psia pressure. From this example it is determined that the azeotropic composition is about 1.5 weight percent 1,1,1,3,3-pentachloropropane at 14.45 psia.

TABLE 1

| WEIGHT PERCENT HCC-240fa (remainder Carbon tetrachloride) | Boiling Point (° C.) at 14.45 psia |
| --- | --- |
| 0 | 77.73 |
| 0.29 | 77.71 |
| 0.86 | 77.71 |
| 1.43 | 77.71 |
| 1.99 | 77.71 |
| 2.55 | 77.71 |
| 3.64 | 77.78 |
| 4.70 | 77.88 |
| 5.74 | 77.90 |
| 6.77 | 77.90 |
| 8.25 | 77.90 |
| 9.70 | 77.91 |

The data also show that the boiling point of mixtures of 1,1,1,3,3-pentachloropropane and carbon tetrachloride is lower or within about 0.2° C., at all indicated blend proportions, than 1,1,1,3,3-pentachloropropane and carbon tetrachloride alone.

What is claimed is:

1. An azeotropic or azeotrope-like composition, which consists essentially of 1,1,1,3,3-pentachloropropane and carbon tetrachloride.

2. The composition of claim 1 having a boiling point of from about 77.7° C. to about 77.9° C. at about 14.4 psia.

3. The composition of claim 2 consisting essentially of from about 0.01 to about 10 weight percent 1,1,1,3,3-pentachloropropane and from about 99.9 to about 90 weight percent carbon tetrachloride.

4. The composition of claim 2 consisting essentially of from about 0.02 to about 5 weight percent 1,1,1,3,3-pentachloropropane and from about 99.8 to about 95 weight percent carbon tetrachloride.

5. The composition of claim 2, which consists essentially of from about 0.05 weight percent to about 3 weight percent 1,1,1,3,3-pentachloropropane and from about 97 to about 99.5 weight percent carbon tetrachloride.

6. A process for separating 1,1,1,3,3-pentachloropropane from an azeotropic or azeotrope-like composition of 1,1,1,3,3-pentachloropropane and carbon tetrachloride comprising the steps of (A) distilling a composition comprising an azeotropic or azeotrope-like composition of 1,1,1,3,3-pentachloropropane and carbon tetrachloride at a first pressure to produce a first overhead stream enriched in either the 1,1,1,3,3-pentachloropropane or the carbon tetrachloride and a first bottoms stream enriched in the other component; and (B) redistilling the first overhead stream at a second pressure to produce a second overhead stream enriched in the component enriched in the first bottoms stream and a second bottoms stream enriched in the component enriched in the first overhead stream.

7. The process of claim 6 wherein said distillation steps are performed as a continuous process.

8. The process of claim 7 wherein said distillation step (A) is performed using a different distillation column than redistillation step (B).

9. A process for removing 1,1,1,3,3-pentachloropropane from a mixture containing 1,1,1,3,3-pentachloropropane and at least one impurity, the process comprising adding carbon tetrachloride to a mixture containing 1,1,1,3,3-pentachloropropane and at least one impurity in an amount sufficient to form an azeotropic or azeotrope-like composition of the 1,1,1,3,3-pentachloropropane and the carbon tetrachloride, and thereafter separating the azeotropic or azeotrope-like composition from the impurity.

10. The process of claim 9 wherein the impurity does not form an azeotropic or azeotrope-like composition with 1,1,1,3,3-pentachloropropane, carbon tetrachloride or a mixture of 1,1,1,3,3-pentachloropropane and carbon tetrachloride.

11. The process of claim 10 wherein the impurity comprises a halocarbon.

12. The process of claim 10 wherein the impurity is miscible with 1,1,1,3,3-pentachloropropane.

13. The process of claim 10 wherein said separating step comprises distillation.

14. The process of claim 10 further comprising the step of separating 1,1,1,3,3-pentachloropropane from an azeotropic or azeotrope-like composition of 1,1,1,3,3-pentachloropropane and carbon tetrachloride using pressure swing distillation.

15. The process of claim 10 wherein the azeotropic or azeotrope-like composition comprises from about 0.01 to about 10 weight percent 1,1,1,3,3-pentachloropropane and from about 90 to about 99.9 weight percent carbon tetrachloride.

16. The. process of claim 15 wherein the azeotropic or azeotrope-like composition consists essentially of from about 0.01 weight percent to about 10 weight percent 1,1,1,3,3-pentachloropropane and from about 90 to about 99.9 weight percent carbon tetrachloride.

17. A method of forming an azeotropic or azeotrope-like composition which comprises combining 1,1,1,3,3-pentachloropropane and carbon tetrachloride in amounts effective and under conditions sufficient to form an azeotropic or azeotrope-like composition consisting essentially of 1,1,1,3,3-pentachloropropane and carbon tetrachloride.

18. A method of forming an azeotropic or azeotrope-like composition, which comprises combining from about 0.01 to about 10 weight percent 1,1,1,3,3-pentachloropropane and from about 90 to about 99.99 weight percent carbon tetrachloride, which composition has a vapor pressure of about 14.4 psia to about 14.7 psia at about a temperature of about 78° C.

19. A method which comprises distilling a mixture comprising 1,1,1,3,3-pentachloropropane and carbon tetrachloride to produce a stream comprising an azeotropic or azeotrope-like composition of 1,1,1,3,3-pentachloropropane and carbon tetrachloride.

* * * * *